US00PP08145P

United States Patent [19]

Holtkamp, Sr.

[11] Patent Number: Plant 8,145

[45] Date of Patent: Feb. 16, 1993

[54] AFRICAN VIOLET PLANTED NAMED LITTLE AZTEC GIRL

[76] Inventor: Reinhold Holtkamp, Sr., Blumenstrasse 28, D 4242 Rees-Haffen, Fed. Rep. of Germany

[21] Appl. No.: 736,639

[22] Filed: Jul. 26, 1991

[51] Int. Cl.[5] ..... A01H 5/00

[52] U.S. Cl. ..... Plt./69.1

[58] Field of Search ..... Plt./69.1, 69.2

*Primary Examiner*—James R. Feyrer

*Attorney, Agent, or Firm*—Foley & Lardner

[57] ABSTRACT

A new and distinct cultivar of African violet named Little Aztec Girl characterized by its mid-size growth habit (13–15 cm in diameter); purplish red, semi-double to double flowers having 8–12 petals, the ones in the center being much smaller and occasionally covering up the anthers; strong stems which curve toward the center to form a compact bouquet above the leaves; profuse flowering; dark green, spear-shaped, serrated and very hairy leaves; flowering 10–11 weeks after planting of unrooted shoot, and by its long lasting and non-dropping flowers.

1 Drawing Sheet

The present invention comprises a new and distinct cultivar of African violet plant, botanically known as *Saintpaulia ionantha*, and hereinafter referred to by the cultivar name Little Aztec Girl.

The new cultivar was referred to during the breeding and selection process by the designation M/I 485 and is a sport of Little Amethyst, disclosed in my U.S. Plant Pat. No. 6,930. Little Aztec Girl is similar in all essential respects to Little Amethyst except for its larger size and lack of white edges around the blossoms.

Little Aztec Girl was discovered in a flowering block of the parent cultivar Little Amethyst and subsequently selected. Asexual reproduction of the new cultivar by leaf cuttings, as performed by me at Haffen, West Germany, has demonstrated that the combination of characteristics as herein disclosed for the new cultivar are firmly fixed and retained through successive generations of asexual reproduction.

Little Aztec Girl has not been observed under all possible environmental conditions. The phenotype may vary significantly with variations in environment such as temperature, light intensity and day length. The following observations, measurements and values describe the new cultivar as grown in a 5.5 cm pot in Haffen, West Germany and Nashville, Tenn. under greenhouse conditions which closely approximate those generally used in commercial practice.

The following traits have been repeatedly observed and are determined to be basic characteristics of Little Aztec Girl, which in combination distinguish this African violet as a new and distinct cultivar:

(1) A single crown will not grow larger than 13–15 cm.

(2) Semi-double to double purplish red flowers.

(3) Strong, wirelike and upright flower stems curving toward the center.

(4) First flash of flowers forms a tight bouquet above the leaves.

(5) Profuse flowering.

(6) Each plant carries 6–8 and more upright flower stems each of which carries 5–7 and more flowers.

(7) Long lasting, non-dropping flowers.

(8) Plant saleable 10 to 11 weeks after planting of unrooted shoot.

(9) Seed capsules push slightly through.

(10) Dark green, hairy leaves.

(11) Spear-shaped leaves are 2.5 to 3.5 cm in size.

(12) After maturity the flowers dry off, and remain on the peduncle without becoming infected by botrytis.

The accompanying color photographic drawing shows a typical specimen plant of the new cultivar grown in a 5.5 cm pot. The colors appearing in the photograph are as true as possible with color illustrations of this type.

In the following description, color references are made to The Royal Horticultural Society Colour Chart (R.H.S.), except where general colors of ordinary significance are referred to. Color values were taken under natural sunlight conditions at approximately 12 p.m. in Nashville, Tenn.

Botanical Classification: *Saintpaulia ionantha*, Ramat., c.v. Little Aztec Girl.

Parentage: Sport of Little Amethyst, disclosed in U.S. Plant Pat. No. 6,930.

Propagation: The new cultivar holds its distinguishing characteristics through successive propagations by leaf cuttings.

Plant: From 6 cm to 8 cm tall when grown in pots, and 13–15 cm in diameter when fully grown.

Leaves:

*General form.*—Spear-shaped.

*Diameter.*—25–30 mm wide and 30–35 mm long.

*Texture.*—Velvety.

*Aspect.*—Serrated, very hairy, shiny.

*Veins.*—Upperside: visible; underside: well pronounced, light green, shiny; on young leaves purplish red.

*Color (upperside).*—Yellow-Green Group 147 A and darker.

*Color (underside).*—Greyed-Purple Group 186 A to B.

*Petiole.*—Strong, purplish brown, hairy.

Flowers:

*Buds.*—Size: 3–5 mm just before opening. Shape: Ball-shaped. Color: Purplish red.

*Sepals.*—Five (5). Color: Purplish brown.

*Calyx.*—Shape: Funnel-shaped. Aspect: Spear-shaped, hairy.

*Peduncle.*—Character: Strong upright, hairy. Color: Purplish brown.

Individual flowers:

*Size.*—25–30 mm.

*Shape.*—Semi-double to double; 8–12 petals per flower. Occasionally the 2–3 small petals in the center cover up the anthers.

*Color (upperside).*—Between Purple Group 78 A and Purple-Violet Group 80 A. Under cooler temperatures and more intensive lighting, the purplish red tends to intensify.

*Color (underside).*—Purple Group 80 C to D.

*Color (underside).*—Purple Group 80 C to D.

*Borne.*—Each flower stem carries 5–7 and more flowers on strong, upright peduncles that are free standing above the leaves, thereby forming a compact bouquet.

*Flowering habit.*—Flowers 10–11 weeks after planting an unrooted plantlet.

Reproductive organs:

Stamens.—Two (2). Anthers: 2 composed of 4 anther cells, seed capsule pushes slightly through.

*Filaments.*—Yellowish green, 2–3 mm long.

*Styles.*—5–6 mm long, purplish red, base of ovary light green and hairy.

Roots: Normally developed, white when young, turning slightly brownish when older.

Disease Resistance: Up to date, Little Aztec Girl has shown very good resistance to all major violet diseases.

GENERAL OBSERVATIONS

Little Aztec Girl is a mid-size violet, a size between a regular violet (grown in a 10 cm pot) and a superminiature (grown in a 4 cm pot). Little Aztec Girl is designed to be grown in a 5.5 cm to 6 cm pot and will not grow larger than 13–15 cm. The semi-double to double flowers are composed of 8–12 petals, the ones in the center being much smaller and occasionally covering up the anthers. The flowers are long-lasting and non-dropping. A nice bouquet of flowers free standing above the leaves develops 10–11 weeks after planting an unrooted plantlet. Each of the 7–8 and more strong flower stems carries 5–7 and more purplish red flowers. The dark green leaves are spear-shaped, serrated and very hairy.

I claim:

1. A new and distinct cultivar of African violet named Little Aztec Girl, as described and illustrated, and particularly characterized by its mid-size growth habit (13–15 cm in diameter); purplish red, semi-double to double flowers having 8–12 petals, the ones in the center being much smaller and occasionally covering up the anthers; strong stems which curve toward the center to form a compact bouquet above the leaves; profuse flowering; dark green, spear-shaped, serrated and very hairy leaves; flowering 10–11 weeks after planting of unrooted shoot, and by its long lasting and non-dropping flowers.

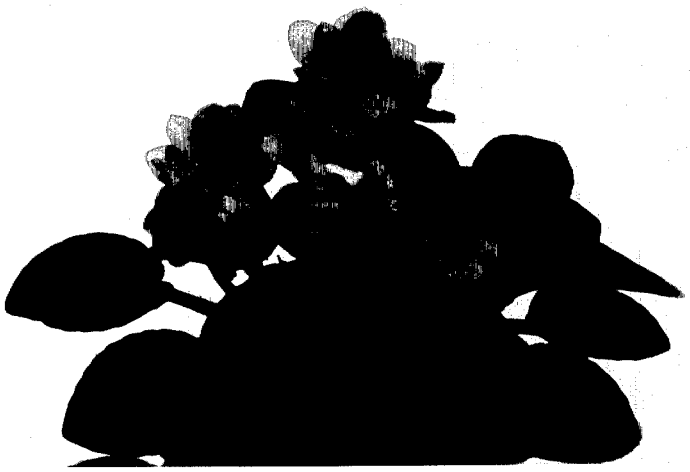

* * * * *